United States Patent [19]
Comai et al.

[11] Patent Number: 6,051,753
[45] Date of Patent: Apr. 18, 2000

[54] FIGWORT MOSAIC VIRUS PROMOTER AND USES

[75] Inventors: Luca Comai, Seattle, Wash.; Margaret P. Sanger; Stephen Daniel Daubert, both of Davis, Calif.

[73] Assignee: Calgene, Inc., Davis, Calif.

[21] Appl. No.: 07/985,742

[22] Filed: Dec. 4, 1992

Related U.S. Application Data

[63] Continuation of application No. 07/431,429, Nov. 3, 1989, abandoned, which is a continuation-in-part of application No. 07/404,283, Sep. 7, 1989, abandoned.

[51] Int. Cl.[7] .............................. C12N 15/34; C12N 5/04; C12N 15/82; A01H 5/00
[52] U.S. Cl. ..................... 800/278; 800/286; 800/298; 435/320.1; 435/419; 435/468; 536/23.72; 536/24.1; 536/24.5
[58] Field of Search ............................. 435/172.3, 320.1, 435/240.1, 468, 419; 800/205, 278, 286, 298; 935/25; 536/24.1, 24.5, 23.72

[56] References Cited

U.S. PATENT DOCUMENTS 4,940,835  7/1990  Shah et al. .............................. 800/205

OTHER PUBLICATIONS

Wu et al., "Comparative Analysis of Caulimovirus Promoters in Protoplasts," *Phytopathology Meetings* (1988) 78:#38.

Richins et al., "Sequence of figwort mosaic virus DNA (caulimovirus group)," *Nucleic Acids Research* (1987) 15:8451–8466.

Shepherd et al., "Figwort mosaic virus: properties of the virus and its adaptation to a new host," *Phytopathology* (1987) 77:1668–1673.

Fang et al., "Multiple cis Regulatory Elements for Maximal Expression of the Cauliflower Mosaic Virus 35S Promoter in Transgenic Plants," *The Plant Cell* (1989) 1:141–150.

Odel et al., "Properties of an isolated transcription stimulating sequence derived from the cauliflower mosaic virus 35S promoter," *Plant Molecular Biology* (1988) 10:263–272.

Ow et al., "Functional regions of the cauliflower mosaic virus 35S RNA promoter determined by use of the firefly luciferase gene as a reporter of promoter activity," *Proceedings of the National Academy of Sciences* (1987) 84:4870–4874.

Nagy et al., "Properties of Expression of the 35S Promoter from CaMV in Transgenic Tobacco Plants," *Biotechnology in Plant Science* (1985) 227–235.

Odell et al., "Identification of DNA sequences required for the activity of the cauliflower mosaic virus 35S promoter," *Nature* (1985) 313:810–812.

Gardner et al., "The Complete nucleotide sequence of an infectious clone of cauliflower mosaic virus by M13mp7 shotgun sequencing," *Nucleic Acids Research* (1981) 9:2871–2881.

Teeri, et al., "Gene Fusions to lacZ Reveal New Expression Patterns of Chimeric Genes In Transgenic Plants," *EMBO J.* (1989) 8(2):343–350.

Ow, et al., "Transient and Stable Expression of the Firefly Luciferase Gene in Plant Cells and Transgenic Plants," *Science* (1986) 234:856–859.

Benfey, et al., "The CaMV 35S Enhancer Contains At Least Two Domains Which Can Confer Different Developmental and Tissue–Specic Expression Patterns," *EMBO J.* (1989) 8(8):2195–2202.

Sanders et al 1987 Nucleic Acids Research 15:1543–1558.

Goldberg et al 1988 Phytopathology 78(12 part 1): 1517 Abstract #37. (Dec.).

Gowda et al (1989) J of Cell Biochem 13D:M318 (Abstract) (Mar.)

*Primary Examiner*—David T. Fox

[57] ABSTRACT

This invention relates to a novel plant promoter derived from the figwort mosaic virus and methods of use of same.

15 Claims, 4 Drawing Sheets

```
   1  GAATTCAGAC  AAATTTGGGA  AAAATCCAGA  TTATCTGATC  TTGAAGATGG  AGTCGCTGAA   60
  61  AAATTCTACA  CAGAAGATAA  AGCTACAAAA  TCCCTCTTCA  CATTCACAGA  AAATGCAGAA  120
 121  CCATATCTTG  TTCATGCAGC  TTTCCGTGCA  GGATTAGCAA  AGTAATCTA   CCCTAGTCCA  180
 181  AATCTCCAAG  AACTCAAATG  GTTCCCAAGA  GATATCGTTA  AGGCAATCAA  ACATTCCGG   240
 241  AAGAAAGTGT  TAAACGCCAA  AGACTCAGCA  ATCTACATCA  AGATTTTCAG  CAGTCTACCA  300
 301  GATTGGAAAC  AATCAGAAAG  GTTCACGCCT  TACCATTTCT  TGCAAATTGG  TATTTCCAAA  360
 361  GCAAAGAAAG  AGCTCCCAAG  CACGAAGGCA  TGTGTCGGAA  AAGATTTTCC  AACCGAGCAG  420
 421  CAGATGGCAG  CAATCAGATC  ATCAAGTCTG  AAAACCATAG  TCGAAAAATT  ACAGGAGATA  480
 481  AAAAATGACT  CAACTGTAAA  AATCAACTAT  GACTCAAGCA  CATGCATCAT  CTCGAGCAAG  540
 541  TGTACAAAAA  AGATTACCAC  GGAAGAAATT  CACAAGGTAA  AACTTTTTGA  GAAAAGATTG  600
 601  ATCAACATCA  ATCAAATCAA  TTGTGGAGAC  CACACAAAGA  AATTGTGGTG  TAAAATTCTA  660
 661  CAGAAAAAGT  ACGAAGAGCA  TCTTTGCCAG  TACTGCAGTG  GGGACCACCC  ACGTGACAAC  720
 721  AAAGAAGTGG  CAGACAAGTC  ACCTCAAAGT  GGAACCCATC  CACGTGATAA  AAGTATCATG  780
 781  GCAGACAGCC  GGTACAATAA  TGGGGAGGAC  AGCTTGCAAA  GCAGCCCATG  TGGAAGCCCA  840
 841  CTCACAAACG  CGTATTACGA  ACGCAGTGAC  GAAGATCATC  CAAGAATTCC  ATCTATTAA   900
 901  AGACGGATTC  ATTCCCATTT  GAAGATCATC  AATACTCAAC  CAATATTTCT  CACTCTAAGA  960
 961  AATAAAGAGC  TTTGTATTCT  TCAATGATAG  GCTAAGACCC  TAAAGAGTCT  CGAAAGAGAC 1020
1021  ATGTAGTATA  GTAAGAGTCC  TCCCAGTCCG  GGAGATTGTA  ATAAAGAGAT  CTTGTTAAGG 1080
1081  ATCC
```

FIGURE 4

FIGWORT MOSAIC VIRUS PROMOTER AND USES

CROSS REFERENCE TO RELATED APPLICATION

This is a continuation of application Ser. No. 07/431,429, filed Nov. 3, 1989, now abandoned, which is a continuation-in-part of U.S. application Ser. No. 07/404,283, filed Sep.7, 1989, now abandoned, which disclosure is incorporated by reference.

This invention was made with Government support under Grant No. 87-CRCR-1-2339 awarded by the U.S. Department of Agriculture. The government has certain rights in this invention.

INTRODUCTION

1. Field of the Invention

The field of this invention relates to novel compositions and method of use of such novel compositions for expression of a DNA sequence of interest in a plant cell.

2. Background

There are two distinct promoters of transcription found in the genomic DNAs of all sequenced members of the caulimovirus group: cauliflower mosaic virus, figwort mosaic virus, and carnation etched ring virus. In cauliflower mosaic virus (CaMV) the 19S promoter lies before viral gene VI and promotes the transcription of that gene. The CaMV 35S promoter lies behind gene VI and promotes transcription of a genome-length RNA which is the template for virus replication.

The 35S promoter of CaMV has seen extensive use as a component of chimeric genes engineered for constitutive expression in transgenic plants. It is highly active, functioning in a wide variety of cell and tissue types in both monocotyledonous and dicotyledonous plants. Three functional regions have been defined for the 35S promoter. These include the two motifs common to RNA polymerase II transcription sites, the TATA and CCACT boxes. A third region containing enhancer elements begins superimposed upon the CCACT box and extends far upstream into the coding region of gene VI.

It is the region of enhancer elements that renders the 35S promoter relatively strong. Some organ and tissue specificity has been reported for the 35S promoter. Benfey et al. (*EMBO*, (1989) 8:2195) suggest that the 35S promoter appears constitutive as a consequence of the contemporaneous operation of a battery of individually organ-specific elements in the enhancer region. These include an element overlapping the CCACT box, with homology to an opine synthase enhancer.

BRIEF DESCRIPTION OF THE DRAWINGS

FIG. 4. The DNA sequence of the 1.1 kb region designated herein as the "full 34S FMV promoter." The 1084 base pair DNA sequence derived from figwort mosaic virus strain M3, contains the core 34S promoter. Sequence reads from 5' end of the segment. Note: TATTTAA box at position 894 and CCACT box at position 838.

SUMMARY OF THE INVENTION

Figure 1:
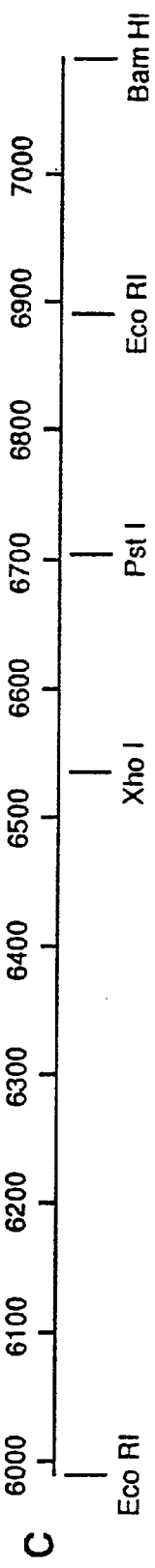
FIGS. 1A–1C FMV strain M3 promoter sequence (middle line) compared with A) CaMV strain 1841 (top line) 34S promoter, and B) FMV strain DXS sequence (bottom line). Comparison in the enhancer region show CCACT (motifs underlined in dashes) and TGACG (underlined) domains. The comparison in the TATA region continues the sequence from above extending to the +1 region. Asterisks (*) indicate nucleotide matches. Putative stop codons for the gene VI reading frame of FMV DxS (≠) and CaMV 1841 (+) are indicated. The transcriptional start for the full length 35S RNA of CaMV (position 7431) is in bold. C) Restriction map of sites used in promoter constructs is shown with coordinates aligned to those of the DxS genome at the Eco RI site at 6886.

In this report we describe a strong promoter analogous to the 35S promoter derived from figwort mosaic caulimovirus (FMV) strain M3. We demonstrate by analogy to the 35S promoter, and by comparison to the regulated mannopine synthase promoter of the *Agrobacterium tumefaciens* transferred-DNA (T-DNA), that the promoter from FMV is constitutively active and not strongly organ specific. It is functionally analogous to the 35S promoter in both transiently expressing protoplasts and stably transformed plants. The 35S promoter is named for the sedimentation coefficient of its product, the genome-length RNA transcript. Since the FMV genome is slightly smaller than that of CaMV we have designated this FMV promoter the "34S" promoter.

DETAILED DESCRIPTION OF THE INVENTION

A segment of DNA from the genome of figwort mosaic virus (FMV) strain M3 possesses promoter activity when tested in electroporated protoplasts from, and transgenic plants of *Nicotiana tabacum* cv. Xanthi nc. The DNA segment studied, designated the "34S" promoter, comprises 1.1 kb from comparable coordinates on the FMV genome to those of the 35S promoter of cauliflower mosaic virus (CaMV). The 34S and 35S promoters show approximately 63% nucleotide homology in the 100 bp adjacent to the 35S transcriptional start site, but in sequences further upstream the homology drops below 50%. Promoter activities were estimated using β-glucuronidase (GUS) and neomycin phosphotransferase II (NPT) reporter gene systems. The activity of the 34S FMV promoter segment is equivalent to 35S promoter activity in both protoplast transient expression assays and in stably transformed tobacco plants. Truncation of 5' sequences from the 34S promoter indicates that promoter strength depends upon DNA sequences located several hundred nucleotides upstream from the TATA box. In leaf tissue the 34S promoter is 20 fold more active than the mannopine synthase (MAS) promoter from *Agrobacterium tumefaciens* T-DNA. The 34S promoter lacks the root-specific expression and wound-stimulation seen for the MAS promoter, showing relatively uniform activity in root, leaf, stem, and floral tissues.

The 34S promoter of figwort mosaic virus is divergent in sequence but has promoter activity equivalent to that of the genome-length transcript promoter in cauliflower mosaic virus, the 35S promoter. This was evident in several areas of comparison: 1) both promoters are located at the same general position relative to viral gene organization, at the border between gene VI and the large caulimoviral intergenic region; 2) each promoter's strength varies with the addition of sequence elements extending hundreds of basepairs upstream from the core promoter domain, and into the coding region of gene VI; 3) core promoter sequences of the 34S and 35S promoters show significant nucleotide sequence homology. The 34S promoter characterized here carries the TATTTAA variation on the consensus TATA box, as does the weaker 19S promoter of CaMV strain Cabb S (Guilley et al., *Cell* (1982) 3:763–773). This and other sequence variations not withstanding, the relative maximal strengths of the 34S and 35S promoters are comparable. Further studies will be necessary to describe the impact of 5'-untranslated leader segments or different polyadenylation sequences upon production rates of RNA transcripts and the activities of the reporter genes they encode.

Glucuronidase activity measurements of 34S function were reproducible among triplicate electroporations with only very little scatter in the data. In contrast, analysis of the activities of various constructs in planta was complicated by the considerable variation encountered between individual transformation events. This variation in activity among independent transformation events is expected in transgenic plants. Transformation-linked events can disparately influence the expression levels of paired genes linked together on the same T-DNA insert, resulting in their non-coordinate expression. These large in planta deviations make it difficult to assess all but the most major differences between promoter constructs, or between different organ expression levels from a given construct.

Nevertheless, the full length 34S promoter appears to be constitutive, or in other words, broadly active, at the plant organ level, showing no marked organ preference. Additionally, its activity was not modulated under conditions where the apparently auxin-responsive mannopine synthase promoter was induced. Our results cannot distinguish whether the slight stimulation in 34S activity seen upon wounding is a property of the promoter, non-specific stimulation of GUS expression due to the altered state of wounded tissue, or stimulation transduced to the GUS gene from the enhancer activity of the adjacent MAS promoter.

The 34S promoter is a valuable additional tool for plant gene engineering in applications calling for twin strong, constitutive promoters in the same transferred DNA cassette. For example, in cases where the use of dual 35S promoters between the same pair of T-DNA borders results in genetic instability due to recombination between identical promoter sequences, the sequence divergence between 34S and 35S promoters may be sufficiently divergent to mitigate such concerns. Further work will be required to test this idea as well as to analyze at more refined levels the expression of 34S in different tissue and cell types and in different species. Availability of the 34S promoter may also increase the degrees of freedom in designing expression vectors for higher plants because of significant variation in promoter/enhancer region sequences in the 34S and 35S promoters.

EXPERIMENTAL

EXAMPLE 1

In this example, the preparation of various promoter constructs (FWP's 100/200, 101/201, 102/202 and 103/203) is described.

The "full length" 34S promoter refers to the entire 1.1 kb EcoRI to BamHI fragment (FIG. 1C). All truncated sequences are coterminal at the BamHI site (FIG. 1C). The full length 34S promoter was subcloned in two steps into pUC12 (Ken Buckley, Ph.D. Thesis, UC San Diego) from the cloned FMV strain M3 genome (Shepherd et al., *Phytopathology* (1987) 77:1668–1673) as a 0.9kb EcoRI fragment and a 0.2 kb EcoRI to BamHI fragment. The two fragments were reassembled as a 1.1 kb segment in pGEM 7 zf(+) (Promega) flanked by a unique XbaI site (5'). The "half length" promoter (549 bp long) derived from the full length by removal of the section between the upstream EcoRI site and an XhoI site 362 bp upstream from the first "T" in TATTTAA. The "quarter length" promoter (383 bp long) was derived from the half length by the removal of a 166 bp section between the XhoI site and a PstI site 196 bp upstream from TATTTAA. The "TATTTAA only" promoter (196 bp long) was derived from the full length by the removal of the section between the upstream EcoRI site and a second EcoRI site located 9 bp upstream from TATTTAA.

For electroporation studies the full length and TATTTAA only promoters were ligated into the pUC derived pCGN7304 as XbaI (5') to BamHI (3') fragments. pCGN7304 contains a promoterless β-glucuronidase coding sequence (GUS) (Jefferson, R. A. *Plant Mol. Biol. Reporter* (1987) 5(4):387–405) followed by a terminator sequence from the 3' end of the mannopine synthase (MAS) gene (T-DNA nucleotides 19239-18462) (Winter et al. *Nucleic Acids Res* (1984) 12:2391–2406) The GUS-MAS 3' fragment of pCGN7304 was flanked by a BamHI site (5') and an XhoI site (3'). Ligations yielded full length 34S-GUS-MAS 3' (pFWP-101) and TATTTAA only 34S-GUS-MAS 3' (pFWP-100). Half length and quarter length promoters were derived from pFWP-101 as an XhoI fragment (pFWP-102) or a PstI to XhoI fragment (pFWP-103) ligated into the pUC derived cloning vector pCGN7328. pCGN642 is a 35S-driven-chloramphenicol acetyltransferase (CAT) gene construct containing the 35S promoter of CaMV strain 1841 (−289 to +113 from transcriptional start [Odell et al., *Nature* (1985) 313:810–812]) linked to the chloramphenicol acetyltransferase gene (from pCM4, Pharmacia) and followed by the 3' polyadenylation region of the T-DNA tml gene (TML 3') (T-DNA nucleotides 11208-9063) (Winter et al., supra). pBI 221.1 has been described by Jefferson (supra) and contains the CaMV 35S promoter-GUS-nopaline synthase polyadenylation region (NOS) in pUC19 (Yanisch-Perron et al., *Gene* (1985) 33:103–119).

The four 34S-GUS-MAS 3' constructs described above were placed into the binary vector pCGN1547 (See, U.S. patent application Ser. No. 07/364,362 filed Jun. 9, 1989). pCGN1547 contains the chimeric neomycin phosphotransferase II gene, MAS 5'-NPT-MAS 3', followed by the pUC18 (Yanisch-Perron et al., supra) multiple cloning site (MCS), all located between T-DNA left and right borders for production of transgenic tobacco plants. The MAS 5' region encompasses T-DNA nucleotides 20806-20128 and the MAS 3' region encompasses nucleotides 18462-19239. The plasmid contains the *Agrobacterium rhizogenes* pRi as well as the *E. coli* pBR 322 origins of replication.

The 34S-GUS-MAS 3' plasmids pFWP-100, pFWP-101, and pFWP-102 were each linearized at a unique XbaI site (bordering the 5' end of the 34S promoter) and placed into the XbaI site of pCGN1547 producing pFWP-200, pFWP-201, and pFWP-202 respectively. The quarter length 34S-GUS-MAS 3' gene was removed as a PstI fragment from pFWP-103 and placed into the PstI site of pCGN1547 producing pFWP-203. The plasmid pFWP-210 consists of a 3.4 kb Asp 718 to PstI fragment from pCGN7000 (See, U.S. patent application Ser. No. 07/339,755 filed Apr. 18, 1989) containing MAS 5'-GUS-MAS 3' (MAS 5' and 3' regions as above) placed into the Asp 718 and PstI sites of pCGN1547. pCGN7348 has the GUS-MAS 3' casette driven by the 35S promoter of CaMV strain 1841 (−941 to +2 region [Odell et a. supra]) (MAS 3' as above) inserted into pCGN1547. Binary vectors were transformed into *Agrobacterium tumefaciens* strain LBA 4404 (Hoekema et al., *Nature* (1983) 303:179–180) by the method of Holstus et al. (Holstus et al., *Mol. Gen. Genet.* (1979) 163:181–187). All *E. coli* constructs were maintained in strain 71.18 (Yanish-Perron et al., supra) and manipulated by standard molecular biology protocols such as those found in Ausbel et al. (Protocol in molecular biology, John Wiley and Sons, NY 1987) and Maniatis et al. (Mol. cloning lab. manual (1982), Cold Spring Harbor Lab., NY).

EXAMPLE 2

In this example, the DNA sequence analysis is described.

Fragments encompassing the 549 bp 34S promoter from the XhoI site to the BamHI site were subcloned into pIC 19H (Marsh et al., *Gene* (1984) 32:481–485). DNA sequencing was performed by the dideoxy chain termination method (Sanger et al., *Proc. Natl. Acad. Sci. US* (1974) 74:5463–5467) on double stranded template using the Sequenase™ DNA sequencing kit of U.S. Biochemicals. The 549 bp segment was completely sequenced in both strands. Computer aided analysis was performed using MicroGeni™ sequence software (Beckman Instruments, Palo Alto, Calif.).

Sequencing of the complete full length 34S promoter was also done using the above protocols. The resulting sequence is shown in FIG. 4.

EXAMPLE 3

In this example, protoplast isolation is described.

Protoplasts were isolated from 3–4 week-old in vitro grown *Nicotiana tabacum* cv. Xanthi nc plants incubated 8 h in darkness prior to use. Leaves (40, approximately 2 cm long×1 cm wide, midrib removed) were placed in 60 ml enzyme solution of 0.04% Pectolyase Y23, 0.42% Onozuka cellulase RS (enzymes from Accurate Chemical and Scientific Corp., Westbury, N.Y.), 0.5% potassium dextran sulfate (Meito Sangyo Co. Ltd.), 6% sorbitol, pH 5.5 and were vacuum infiltrated to 0.3 torr followed by a slow return to atmospheric pressure over about 15 min. Leaves were then incubated in the enzyme solution for 3.5 h in darkness at 25°. Protoplasts were separated from debris by filtration through 52 µm nylon mesh, centrifuged at 200×g for 4 min, and washed 3× in 7% sorbitol, 1 mM $CaCl_2$, 10 mM Hepes, pH 5.5.

EXAMPLE 4

In this example, an electroporation study is described.

The electroporation protocol was modified from Fromm et al. (*Proc. Natl. Acad. Sci. USA* (1985) 82:5824–5828) as follows. Protoplasts (3×10$^6$/sample) were resuspended in 0.9 ml electroporation buffer (10 mM Hepes, pH 7.1, 140 mM NaCl, 5 mM $CaCl_2$, 6% sorbitol). Immediately prior to electroporation, the protoplasts were mixed with 100 µl electroporation buffer containing 175 µg pUC 19 carrier DNA, 10 µg pCGN642, and with or without pFWP plasmids. The amount of pFWP DNA used was normalized for differences in plasmid sizes so that each sample received the same molar amount (equivalent to 25 µg pFWP-101). Electroporation was done in 1 ml plastic cuvettes equipped with aluminum foil electrodes (0.5 cm apart) with a 1250 µFarad capacitor at 285 V and a discharge pulse length of 60 ms. Following electroporation the protoplasts were left undisturbed for 5 min and then placed in petri plates containing 9 ml pH 5.5 MS medium (Murashige, T. & Skoog, F., *Physiologia Plantarum* (1962) 15:473–497), sorbitol (5.5%), naphthaline acetic acid (0.6 µg/ml), 2,4-dichlorophenoxyacetic acid (0.2 µg/ml), and kinetin (0.8 µg/ml). The electroporated protoplasts were incubated for 40 h at 25° in darkness prior to extraction and assay.

EXAMPLE 5

In this example, the preparation of transgenic plants is described.

Transgenic *Nicotiana tabacum* cv. Xanthi nc were produced by *Agrobacterium tumefaciens* leaf disk cocultivation as described by Comai et al. (*Nature* (1985) 317:741–744). Following regeneration, rooted plants were placed in soil and the pots covered with plastic film. The film covering was slowly loosened in stages over a 1 week period to allow the young plants to harden. Plants were grown in growth chambers at 28°, 50% relative humidity, with 16 h light (128µE/s-m$^2$ photosynthetically active light) from cool white fluorescent tubes per 24 h period. Approximately 15 transformants were produced for each construct and between 8 to 15 individual transformants were analyzed for each construction.

EXAMPLE 6

In this example, tissue extraction is described.

Leaf tissue (15–200 mg) was ground (1 ml buffer/g fr. wt.) with 50 mM Tris-HCl, pH 6.8 containing 71 mM 2-mercaptoethanol, 1 µg/ml leupeptin, and 20% (v/v) glycerol in a 1.5 ml conical plastic microfuge tube using a plastic pestle. The tubes were centrifuged at 12,000×g for 4 min at 4° and the supernatant was used as extract for enzyme assays.

Protoplasts were collected from incubation medium by centrifugation (900×g, 8 min). Each pelleted protoplast sample was resuspended in 400 µl 50 mM Tris-HCl, pH 7.8 containing 10 mM 2-mercaptoethanol, 1 µg /ml leupeptin and 20% (v/v) glycerol and lysed by sonication (20 s, 400 W, Braun-sonic model 1510, 0.5 cm diameter probe).

EXAMPLE 7

In this example, various enzyme assays and protein determinations are described.

Extract β-glucuronidase activity was determined by the fluorometric assay of Jefferson (supra) with detergents omitted from the assay buffer. Incubations were at 37° for 30 min. The 4-methylumbelliferyl-β-D-glucuronide was from Molecular Probes Inc., Eugene, Oreg. Methylumbelliferone and β-glucuronidase were from Clontech Laboratories, Inc., Palo Alto, Calif.

Extract neomycin phosphotransferase II activity was determined by the dot blot method of McDonnell (McDonnell et al., *Plant Mol. Biol. Reporter* (1987) 5:380–386). Assay conditions were 30° for 30 min. The blotted samples were cut apart and quantification was by liquid scintillation counting.

Extracts were assayed for chloramphenicol acetyltransferase activity using the radiolabeled method of Gorman et al. (*Mol. and Cell Biol.* (1982) 2:1044–1051). Prior to assay extracts were incubated 10 min at 65° (Fromm et al., supra). Reactions were incubated for 15–30 min at 37°. Monoacetylated and di-acetylated chloramphenicol were produced by reacting chloramphenicol (62 μmol) with acetic anhydride (64 μmol) in pyridine (1 ml) for 15 min at 100° in a sealed glass vial. The reaction products were dried under vacuum and resuspended in methanol to yield a mixture of chloramphenicol, 1- and 3-monoacetyl chloramphenicol, and 1,3-diacetyl chloramphenicol (Burzio et al., *Gene Anal. Techn.* (1988) 5:5–8). Assay products were separated from unreacted substrate by thinlayer chromatography and quantified using an AMBIS radioanalytic imaging system (Automated Microbiology Systems, Inc).

Protein concentrations were determined by the method of Bradford, M. M. (*Anal. Biochem* (1976) 72:248–254) using a microplate reader equipped with a 595 nm filter as described by BioRad (BioRad Bulletin 1177 (1984)).

EXAMPLE 8

In this example, a comparison of the 34S from figwort and the 35S from CaMV is provided.

Figwort mosaic virus was isolated from *Scrophularia californica* in the Pajaro valley, Monterey county, Calif. Strains M3 and DxS have been recovered from this isolate (Shepherd et al., *Phytopathology* (1987) 77:1668–1673). The nearly 20% sequence divergence with 549 bp of 34S promoter (26% sequence divergence with the entire 1084 bp 34S promoter) seen between the promoter regions of these two strains (FIG. 1B) contrasts markedly with conservation in CaMV 35S promoters. Among the five isolates of CaMV for which the sequence is known, the region is completely conserved in three cases (Balazs et al. *Gene* (1982) 19:239–249; Gardner et al. *Nucleic Acids Research* (1981) 9:2871–2881; Franck et al., *Cell* (1980) 21:285–294) and off at only 1 position in the fourth example (Fang et al., *Chinese Journal of Virology* (1985) 1:247–256); the Bari isolate (Stratford et al., *Journal of General Virology* (1988) 69:2375–2386) is reportedly 10% different at the positions shown in the FIG. 1. The 34S promoter from FMV strain M3 was found to contain a non-consensus TATA box (FIG. 1). Sequence comparison between the 34S and 35S promoters revealed extensive homologies through their CCACT, TATA, and −18 to +1 domains. They differed at only approximately 37% of the positions shown in FIG. 1A. However, beyond these relatively conserved domains the two sequences showed much less homology. Within the 549 bp pFWP-102 promoter segment they showed only 47% identity, as maximized by computer-aided inclusion of 36 gaps. In contrast, comparison of the two FMV strains over the same 549 bp region showed 71% nucleotide matches, approximately the same level of homology as seen in the CCACT, TATA, and −18 to +1 domains (FIG. 1B).

A 17 bp enhancer element within the 35S promoter is defined by perfectly repeated TGACG motifs (Benfey et al., *EMBO* (1989) 8:2195–2202) the first of which is at position 7351. However, in the corresponding position overlaping the CCACT box of FMV, the sequence is a variation of the CaMV motif (FIG. 1). In FMV the canonical enhancer element appears to be shifted 12 pb downstream relative to CaMV. Analysis of the M3 reading frame shows that, as has been inferred for DxS (Richins et al., *Nucleic Acids Res.* (1987) 15:8451–8466), the stop codon embedded in the TATA box is apparently the terminator codon for gene VI.

EXAMPLE 9

In this example, activity of the 34S promoter in protoplasts is described.

The GUS gene encoded enzyme activity promoted by the series of 5'-truncated 34S promoter sequences in transient expression assays is shown as GUS activity normalized against CAT activity (Table 1).

TABLE 1

Strengths of modified 34S promoters active in electroporated tobacco leaf protoplasts. Promoter strength is given as the ratio of 34S promoter-mediated GUS activity to 35S promoter-mediated CAT activity.

| Plasmid | Promoter[c] | GUS/CAT[a] (mean[b]) | (mean deviation) |
|---|---|---|---|
| pFWP-100 | 34S TATA only | 0.01 | 0.003 |
| pFWP-103 | 34S 1/4 Length | 1.13 | 0.037 |
| pFWP-102 | 34S 1/2 Length | 1.11 | 0.023 |
| pFWP-101 | 34S Full Length | 1.55 | 0.103 |
| pBI-221 | 35S | 0.98 | 0.090 |

[a]GUS/CAT ratios represent pMoles methylumbelliferone produced/cpm total acetylated chloramphenicol produced. Assays and conditions were as described in methods.
[b]Means represent 3 samples.
[c]Numbering from first "T" in TATA CAT activity was derived from a co-electroporated plasmid (pCGN642) carrying a chimeric CAT gene. The TATA only construct, pFWP-100, had negligible GUS activity while the promoter strengths of the half and quarter length constructs were about 70% that of the full length promoter, pFWP-101. The 35S-GUS construct of Jefferson (supra), pBI-221.1, was only about 63% as active as pFWP-101. This construct has a 3' region derived from the nopaline synthase gene, however, so that conclusive quantitative comparisons between 35S and 34S activities in Table 1 are not possible.

EXAMPLE 10

In this example, the activity of 34S in transgenic tobacco is described.

The performance of 34S-GUS-MAS 3' constructs in planta was measured as β-glucuronidase activity normalized against leaf extract protein concentration (Table 2).

TABLE 2

Comparison of the 34S, 35S, and MAS promoters in transgenic tobacco plants. GUS activity was determined using the fluorometric assay of Jefferson (supra) in extracted leaf tissue from incompletely expanded leaves (average size: 8 cm long x 5 cm wide) located from the eighth to sixteenth nodes.

| Construct | Promoter | Methylumbelliferone (nMol/mg protein-min) | Deviation | # of Analyzed[a] |
|---|---|---|---|---|
| pFWP-200 | 34S TATA | 0.01 | 0.00 | 8 |
| pFWP-203 | 34S 1/4 Length | 4.79 | 2.83 | 14 |
| pFWP-202 | 34s 1/2 Length | 6.72 | 5.05 | 8 |
| pFWP-201 | 345 Full Length | 11.01 | 4.48 | 11 |
| pCGN 7348 | 35S | 9.03 | 5.05 | 15 |
| pFWP-210 | MAS | 0.52 | 0.31 | 11 |

[a]numbers represent only plants containing GUS activity > 3 pMol/mg protein-min.

Expression levels of these 34S promoter constructs in stably transformed plants were comparable to the results from the protoplast transient expression system. In both cases activity was enhanced in constructs carrying longer upstream regions. Activity of the full length 34S promoter, pFWP-201, was equivalent to the 35S promoter construct (35S-GUS-MAS 3', pCGN 7348). Both 34S and 35S segments extend more than 900 bp upstream from TATA but the constructions differ in that in the 34S constructions the untranslated leader is inferred to be 156 bp long whereas in the pCGN 7348 the untranslated leader is 9 bp. The full length 34S promoter construct (pFWP-201) showed activity 20 fold greater than that of MAS 5'-GUS-MAS 3' (pFWP-210). The 5' deleted 34S promoter constructs increased in activity with increasing promoter length.

Variation was typically 50% of the mean activity in data from transgenic plants. This might be ascribed in part to differences in the gene expression potentials from chromosomal T-DNA insertion sites. We attempted to correct for this effect by normalizing the various GUS activities against the corresponding kanamycin phosphotransferase (NPT) activities of the closely linked, MAS-driven NPT gene. This treatment of the data still resulted in variations 50% or more of the mean. Since the ratios of GUS to NPT activities from plants containing linked GUS and NPT genes were not constant, there appeared to be factors that affected GUS expression other than the general chromosomal locations of the T-DNA insertions. Though we have no evidence for modulation of basal levels of the MAS promoter activity in leaf tissue, this is an inducible promoter which may compromise its use as an expression level reference.

The variation in GUS and NPT levels between independent transformation events may reflect factors manifest over distances as small as single genes. This is suggested in the percent disjunction (Table 3) we observed between the activities of the closely linked chimeric NPT and GUS genes and in the variable GUS to Kn ratios observed above. In the various constructs the two genes were from 1 to 3 kb apart in the transferred-DNA.

TABLE 3

Disjunction of expression of paired, co-transformed genes. Plants were scored positive for GUS expression if >5 pMol MU/mg protein - min was produced. Plants were scored positive for NPT expression if > 0.1 pMol KP/mg protein - min was produced.

| Expression | No. of Plants[a] | % |
| --- | --- | --- |
| GUS−/KPT+ | 7 | 7.4 |
| GUS+/KPT− | 3 | 3.1 |
| GUS−/KPT− | 6 | 6.3 |
| GUS+/KPT+ | 79 | 83.2 |

[a]This table includes data for some transformants not described in Table 2.

This disjunction rate is similar to the 25% encountered by Fang et al. (*The Plant Cell* (1989) 1:141–150).

EXAMPLE 11

In this example, the activity of the 34S promoter in transgenic tobacco is compared with the activity of a MAS promoter.

Figure 2:
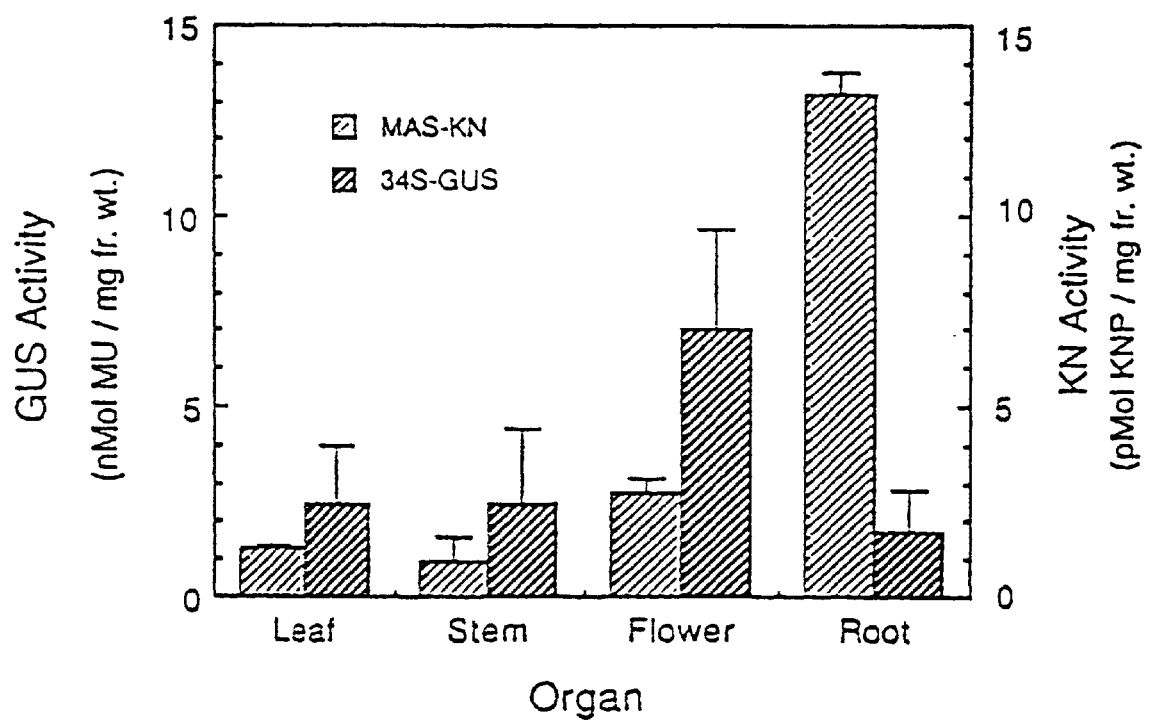
FIG. 2. The 34S promoter-mediated activity and MAS promoter-mediated activity in various tobacco plant organs. Tissue from leaf, stem, root, and flower of mature transgenic tobacco plants containing the linked MAS 5'-NPT-MAS 3' and the 34S-GUS-MAS 3' chimeric genes were extracted and assayed for both GUS and NPT activities. Light columns show mean GUS activity and dark columns represent mean NPT activity. Error bars indicate the standard deviations of 2–5 plants.

The transformed plants described above carried the MAS 5'-NPT-MAS 3' gene linked to the 34S-GUS-MAS 3' gene. This linkage presented a system in which to assess the potential for modulation of the 34S promoter in comparison with the activity of an adjacent, inducible gene. The MAS 5'-controlled NPT gene in pFWP-201 exhibited a definite organ specificity. The NPT activity in roots was eight fold higher than in aerial organs (FIG. 2). By comparison, the linked 34S promoter activity did not show marked tissue tropism.

The data in FIG. 2 could be normalized against tissue fresh weight (shown) or, alternatively, against tissue protein content. Protein content of roots and stems on a fresh weight basis was several fold lower than that of leaves and flowers. Normalization to protein content gave higher root and stem activity, relative to leaves and flowers, as has also been calculated for 35S activity. Thus apparent organ-specific promoter activity can depend upon the chosen mode of normalization.

Figure 3:
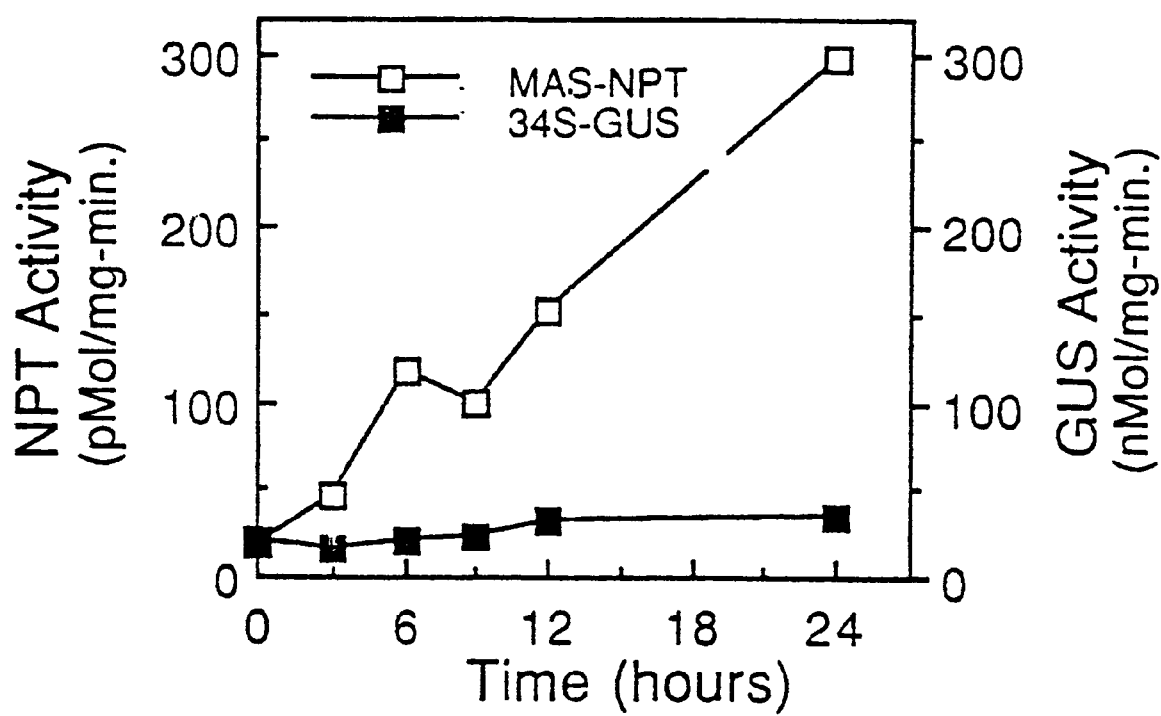
FIG. 3. Effect of wounding on 34S promoter and MAS promoter mediated activities. A transgenic tobacco plant containing the MAS-NPT and 34S-GUS genes (pFWP-201) was wounded by pinching the lamina of its fourteenth leaf with hemostats at 1 cm intervals across the length of the leaf. Both GUS and NPT activities were measured at wound sites at increasing time intervals.

The NPT activity driven by the MAS promoter in roots was neither increased by wounding or decreased by growing roots in a non-abrading environment, in this case, water. However, MAS 5'-NPT activity of pFWP-201 was wound inducible in leaves (FIG. 3). The 34S-GUS activity measured from the same leaf extracts showed no more than a two fold stimulation.

EXAMPLE 12

In this example, the preparation of a gene construct employing 35S and 34S plant viral promoters is described.

An EcoRI-BamHI fragment of a Satellite dimer as described in Gerlarch, W. L., et al., (*Virology* (1986) 157:172–185) is inserted into the BamHI-SstI site of a modified pCGN2113 vector. The modified pCGN2113 (See, U.S. patent application Ser. No. 07/225,332 filed Jul. 27, 1988) contains an inserted XhoI-BamHI 34S, FMV promoter fragment from pFWP-101 and a tml 3' transcript termination region separated by linkers. The newly constructed 34S-dimer-tml is excised by XhoI digestion and inserted into a pCGN1547 PstI site. pCGN1547 contains a 35S-kanamycin resistance gene-MAS 3' in an Agrobacterium binary vector, and is further described in U.S. patent application Ser. No. 07/364,362 filed Jun. 9, 1989. The resulting construct will contain both a 5' 35S-kan-mas 3' and a 5' 34S-dimer-tml 3'.

It is evident from the above results that the figwort mosaic virus promoter contains sequences useful to the genetic engineering of plants. Through recombinant DNA technology, the 34S promoter may be used to initiate transcription at relatively high levels of a heterologous DNA sequence of interest at levels similar to that observed with DNA sequences under the regulatory control of the CaMV 35S promoter. The 34S FMV is expected to find particular application in plants which are host plants of the virus. In light of their similar expression levels and because the FMV and CaMV are related as members of the caulimovirus group, the 34S FMV promoter is an alternative to 35S CaMV promoter and is also expected to find application in those plant cells, tissue and whole plants in which the 35S CaMV promoter is useful. Additionally, for example, in situations where a gene construct requires two strong, yet distinct promoters, the 34S FMV and 35S CaMV promoters may be used together, reducing the potential for spontaneous homologous recombination.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A recombinant DNA construct capable of transcription in a plant cell comprising in the 5' to 3' direction of transcription as operably joined components, a figwort mosaic virus 34S promoter, a DNA sequence of interest heterologous to said promoter and a transcript termination region functional in a plant cell wherein said figwort mosaic virus 34S promoter is at least a quarter length promoter.

2. The recombinant DNA construct of claim 1 wherein said transcript termination region is from the 3' flanking region of the mannopine synthase gene.

3. The recombinant DNA construct of claim 1 wherein said figwort mosaic virus 34S promoter comprises a TATA box having the sequence TATTTAA.

4. The recombinant DNA construct of claim 1 wherein said figwort mosaic virus 34S promoter comprises at least 196 bp 5' of the TATTTAA at nucleotides 894 to 900 of FIG. 4.

5. The recombinant DNA construct of claim 1 wherein said figwort mosaic virus 34S promoter comprises at least 362 bp 5' of the TATTTAA at nucleotides 894 to 900 of FIG. 4.

6. The recombinant DNA construct of claim 1 wherein said figwort mosaic virus promoter comprises at least 892 bp 5' of the TATTTAA at nucleotides 894 to 900 of FIG. 4.

7. The recombinant DNA construct of claim 1 wherein said DNA sequence of interest is a structural gene.

8. The recombinant DNA construct of claim 1 wherein said DNA sequence of interest is an anti-sense DNA sequence.

9. A DNA cassette for plant genetic engineering applications, wherein said DNA cassette comprises a recombinant DNA construct of claim 1, and a second recombinant DNA construct comprising as operably joined components in the 5' to 3' direction of transcriptions, a CaMV 35S promoter, a DNA sequence of interest and a transcript termination region functional in a plant cell.

10. The DNA cassette of claim 9 wherein said DNA sequence of interest joined to said CaMV 35S promoter is different from said DNA sequence of interest joined to said figwort mosaic virus promoter.

11. The recombinant DNA construct of claim 1 further comprising a 5' untranslated leader sequence.

12. The recombinant DNA construct of claim 11, wherein said 5' untranslated sequence is from a figwort mosaic virus 34S promoter.

13. A plant cell comprising a recombinant DNA construct of any one of claims 1, 2–8, 11 and 12 or a DNA cassette of any one of claims 9 and 10.

14. A plant comprising a recombinant DNA construct of any one of claims 1, 2–8, 11 and 12 or a DNA cassette of and one of claims 9 and 10.

15. The recombinant DNA construct of claim 1 wherein said figwort mosaic virus 34S promoter is selected from the group consisting of a quarter length promoter, a half length promoter, and a full length promoter.

* * * * *

UNITED STATES PATENT AND TRADEMARK OFFICE
CERTIFICATE OF CORRECTION

PATENT NO : 6,051,753
DATED    : April 18, 2000
INVENTOR(S): Luca Comai, et al.

It is certified that error appears in the above-identified patent and that said Letters Patent are hereby corrected as shown below:

On title page, Item 73, Assignees replace "Calgene, Inc., Davis, Calif."
with - "Calgene, Inc., Davis and The Regents of the University of California ,Oakland, both of Calif.-"

Signed and Sealed this

Twenty-fourth Day of April, 2001

Attest:

NICHOLAS P. GODICI

Attesting Officer

Acting Director of the United States Patent and Trademark Office